(12) United States Patent
Winkler et al.

(10) Patent No.: US 11,951,023 B2
(45) Date of Patent: Apr. 9, 2024

(54) HARNESS FOR COUPLING TO AN UPPER ARM PROSTHESIS, AND SYSTEMS AND METHODS OF MAKING AND USING SAME

(71) Applicant: United States Government as Represented by the Department of Veterans Affairs, Washington, DC (US)

(72) Inventors: Sandra L. Winkler, Lithia, FL (US); Samuel Phillips, Tampa, FL (US); Jemy Delikat, Brandon, FL (US)

(73) Assignee: United States Government As Represented By The Department Of Veterans Affairs, Washington, DC (US)

( * ) Notice: Subject to any disclaimer, the term of this patent is extended or adjusted under 35 U.S.C. 154(b) by 94 days.

(21) Appl. No.: 17/543,251

(22) Filed: Dec. 6, 2021

(65) Prior Publication Data

US 2022/0175560 A1 Jun. 9, 2022

Related U.S. Application Data

(60) Provisional application No. 63/121,609, filed on Dec. 4, 2020.

(51) Int. Cl.
*A61F 2/80* (2006.01)
*A41C 3/00* (2006.01)
*A61F 2/78* (2006.01)

(52) U.S. Cl.
CPC .............. *A61F 2/80* (2013.01); *A41C 3/0057* (2013.01); *A61F 2002/7862* (2013.01)

(58) Field of Classification Search
CPC ................ A61F 2002/7862; A61F 2/80; A61F 2002/7893; A61F 2/54; A61F 2/581
See application file for complete search history.

(56) References Cited

PUBLICATIONS

Harness Patterns for Upper-Extremity Prostheses, 35 pages, http://www.oandplibrary.org/al/pdf/1955_03_026.pdf (Year: 1955).*

* cited by examiner

*Primary Examiner* — Bruce E Snow
(74) *Attorney, Agent, or Firm* — Ballard Spahr LLP (57) ABSTRACT

A prosthesis system can comprise an upper arm prosthesis comprising a socket, the upper arm prosthesis being positioned on a first side of the prosthesis system proximate a residual limb of a user. A harness that can be coupled to the socket of the upper arm prosthesis. The harness can comprise a front portion that is configured to extend across the chest of the user and receive at least a portion of the breasts of the user therein and a back portion that is configured to extend across the back of the user and couple to opposed lateral sides of the front portion. A first end of a support strap can couple to the socket of the prosthesis at a first anchor point, and a second end can couple to the back portion of the harness on a second side of the prosthesis system opposite the first side.

18 Claims, 10 Drawing Sheets

(Prior Art)

FIG. 1

(Prior Art)

FIG. 2

(Prior Art)

HARNESS FOR COUPLING TO AN UPPER ARM PROSTHESIS, AND SYSTEMS AND METHODS OF MAKING AND USING SAME

CROSS-REFERENCE TO RELATED APPLICATIONS

This application claims priority to and the benefit of the filing date of U.S. Provisional Application No. 63/121,609, filed Dec. 4, 2020, the entirety of which is hereby incorporated by reference herein.

FIELD

The application is generally related to upper limb prostheses and, in particular, to harnesses for attaching the prostheses to a user.

BACKGROUND

Figure 1:
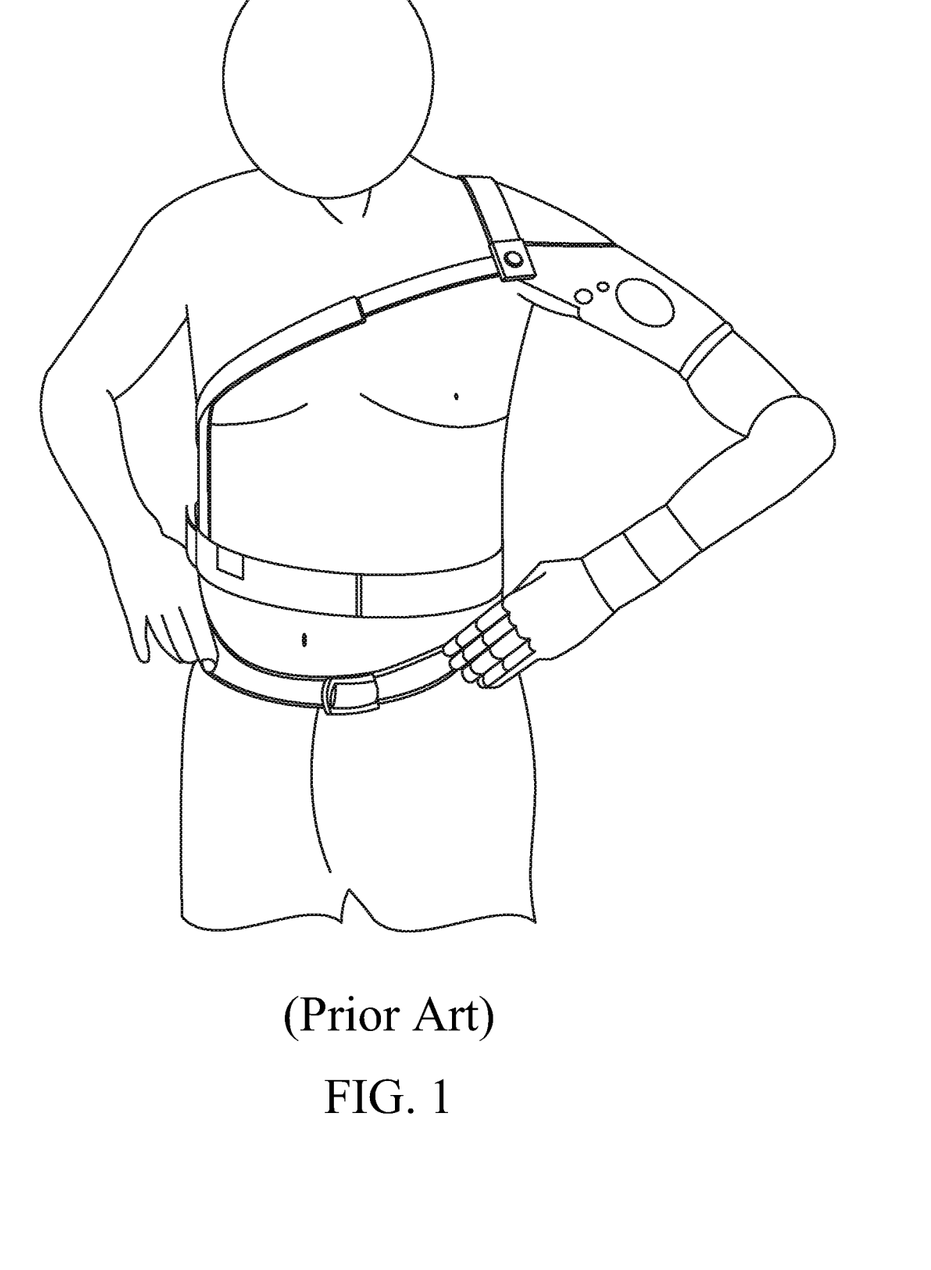
FIG. 1 is a perspective view of a conventional attachment harness for an upper limb prosthesis.
Figure 2:
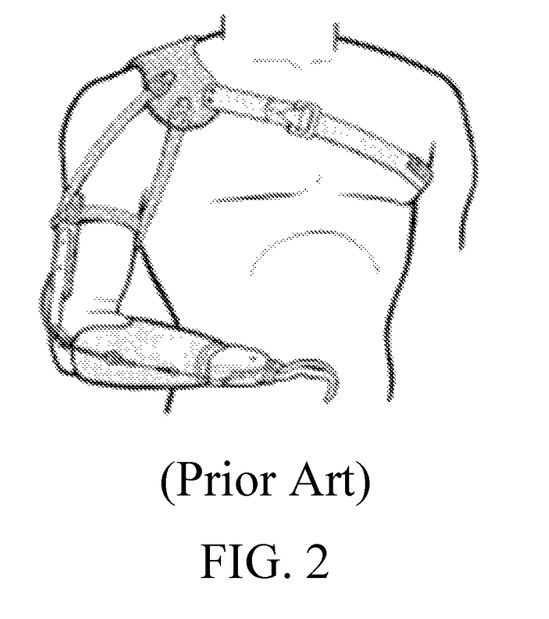
FIG. 2 is a perspective view of another conventional attachment harness for an upper limb prosthesis.
Figure 3:
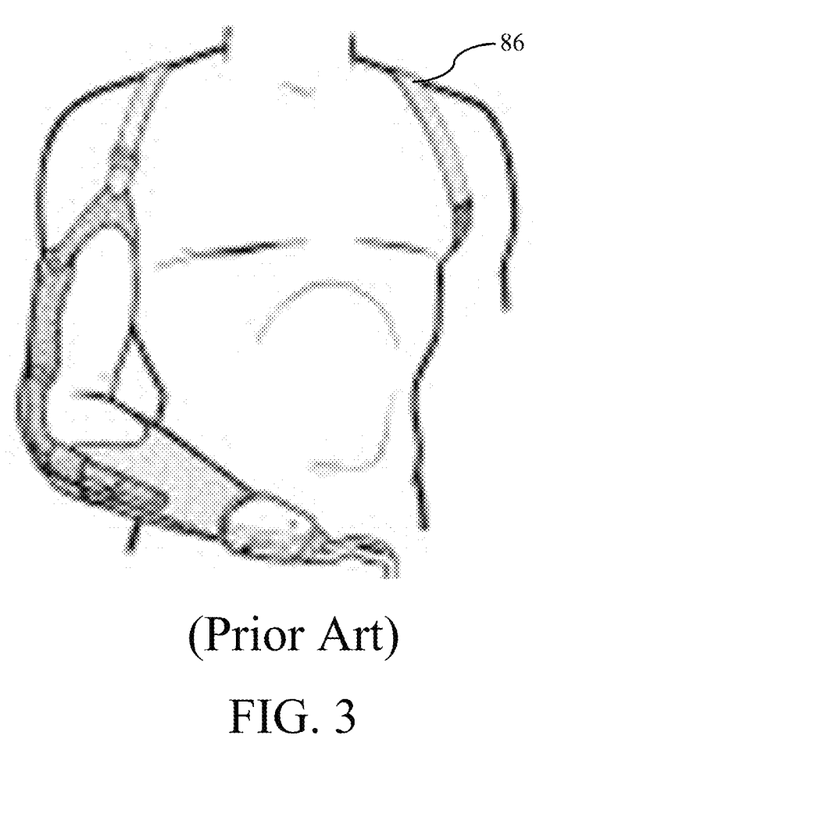
FIG. 3 is a perspective view of yet another conventional attachment harness for an upper limb prosthesis.

Upper limb prostheses, such as those for users with amputations above the elbow or in the shoulder girdle area, typically rely on a conventional attachment harness to attach the prosthesis to the user. As shown in FIGS. 1 and 2, the conventional attachment harness extends across, and distributes load against, the breast of the wearer. FIG. 3 illustrates an alternative embodiment of the conventional attachment harness that distributes essentially all of the weight of the prosthesis to the armpit of the intact arm. Accordingly, the conventional harnesses can be uncomfortable or painful, cosmetically unappealing, damaging to the breast tissue and/or armpit area of the intact arm, and otherwise undesirable. In particular, excessive pressure on breast tissue can disrupt blood flow to the breast, resulting in swelling, significant blood loss, hematoma, fat necrosis, and oil cyst hematoma. Injury to the mammary ducts can affect future or current flow of breast milk. These undesirable qualities can be particularly pronounced for female users. More commonly, injury to smaller superficial arteries and veins can lead to bleeding and bruising. Accordingly, a need exists for a more comfortable, cosmetically appealing alternative to conventional attachment harnesses.

SUMMARY

Described herein, in various aspects, is a prosthesis system for a user having a back, a torso, a chest, breasts, a first side, an opposed second side relative to a sagittal plane, and an upper residual limb on the first side. The prosthesis system can comprise an upper arm prosthesis comprising a socket, the upper arm prosthesis being positioned on a first side of the prosthesis system corresponding to the first side of the user. A harness can be coupled to the socket of the upper arm prosthesis. The harness can comprise a front portion that is configured to extend across the chest of the user and receive at least a portion of the breasts of the user therein, the front portion having opposed lateral sides. A back portion can be configured to extend across the back of the user and couple to the opposed lateral sides of the front portion. A support strap can have a first end and a second end. The first end of the support strap can couple to the socket of the prosthesis at a first anchor point. The second end can couple to the back portion of the harness on a second side of the prosthesis system corresponding to the second side of the user, the second side of the prosthesis system being opposite the first side of the prosthesis system relative to the sagittal plane.

In some aspects, a harness can be for coupling a prosthesis to a user having a back, a torso, a chest, breasts, and an upper residual limb on a first side of the user, the harness having opposing first and second sides divided by a sagittal plane, the first side of the harness corresponding to the first side of the user. The harness can comprise a front portion that is configured to extend across the chest of the user and receive at least a portion of the breasts of the user therein, the front portion having opposed lateral sides. A back portion can be configured to extend across the back of the user and couple to the opposed lateral sides of the front portion. A support strap can have a first end and a second end. The first end of the support strap can be configured to couple to a socket of the prosthesis at a first anchor point on the first side of the harness. The second end can couple to the back portion on the second side of the harness.

In some aspects, a harness can be configured to attach a prosthetic arm to a user having a chest and a residual limb. The harness can comprise a bra that is configured to extend across the chest of the user. A socket can be configured to mate with the residual limb of the user. The socket can be configured to be attached to a prosthesis. At least one coupling member can couple the bra to the socket.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

These and other features of the preferred embodiments of the invention will become more apparent in the detailed description in which reference is made to the appended drawings wherein:

In FIGS. 1, 4-7, and 9-10, dark areas have been added over the faces of the depicted subjects to block out facial features from the original source images.

DETAILED DESCRIPTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a," "an," and "the" include plural referents unless the context clearly dictates otherwise. For example, use of the term "a strap" can refer to one or more of such straps, and so forth.

All technical and scientific terms used herein have the same meaning as commonly understood to one of ordinary skill in the art to which this invention belongs unless clearly indicated otherwise.

As used herein, the terms "optional" or "optionally" mean that the subsequently described event or circumstance may or may not occur, and that the description includes instances where said event or circumstance occurs and instances where it does not.

As used herein, the term "at least one of" is intended to be synonymous with "one or more of." For example, "at least one of A, B and C" explicitly includes only A, only B, only C, and combinations of each.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Optionally, in some aspects, when values are approximated by use of the antecedent "about," it is contemplated that values within up to 15%, up to 10%, up to 5%, or up to 1% (above or below) of the particularly stated value can be included within the scope of those aspects.

The word "or" as used herein means any one member of a particular list and, except where otherwise indicated, can also include any combination of members of that list.

It is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

The following description supplies specific details in order to provide a thorough understanding. Nevertheless, the skilled artisan would understand that the apparatus, system, and associated methods of using the apparatus can be implemented and used without employing these specific details. Indeed, the apparatus, system, and associated methods can be placed into practice by modifying the illustrated apparatus, system, and associated methods and can be used in conjunction with any other apparatus and techniques conventionally used in the industry.

The socket can be the crucial junction where the soft tissue of the user's residual limb interfaces with the rigid materials of the prosthesis. The socket fit can accommodate the anatomy (e.g., female anatomy) of the subject and position the prosthetic device to efficiently transmit intended movements. The socket fit can also include or provide appropriate distribution of pressure across the residual limb. While compression can increase mechanical stability, it can also cause discomfort, tissue irritation, and damage. This challenge is increased for individuals with proximal amputations as the weight of the prosthesis amplifies the demand of the socket and the residual limb.

Disclosed herein, and with reference to FIGS. 5-10, is a prosthesis system 4 comprising an upper limb prosthesis 10 and a harness 20. The upper limb prosthesis 10 can be used by a user 100 having a back 102, a torso 104, a chest 106, breasts 108, an upper residual limb 110 on a first side 112, and an opposed second side 114 relative to a sagittal plane 116. A frontal plane 118 that passes through the body of the user 100 can separate a front 120 of the user from a rear 122 of the user. The prosthesis system 4 can have a first side 6 corresponding to the first side 112 of the user and a second side 8 corresponding to the second side 114 of the user and opposite the first side of the prosthesis system relative to the sagittal plane 116. The prosthesis system 4 can further have a front side and a rear side that correspond, respectively, to the front and rear sides 120, 122 of the user.

The upper limb prosthesis 10 can comprise a socket 12. The upper arm prosthesis 10 can be positioned on the first side 6 of the prosthesis system 4.

In exemplary aspects, the upper limb prosthesis 10 can be a functional prosthesis. A functional prosthesis should be understood to include functional features beyond mere aesthetic features. Optionally, the upper limb prosthesis can comprise a hook, a hand, actuatable grippers, or combinations thereof. For example, the functional prosthesis can comprise or permit mechanical elbow articulation and/or mechanical hand or other gripper articulation. Optionally, the prosthesis 10 can comprise a power source and one or more motors or other actuators. For example, in some aspects, the prosthesis 10 can comprise a first actuator that is configured to actuate a mechanical elbow about a rotational axis and at least one second actuator that is configured to open and close a mechanical hand. In further aspects, the elbow can selectively be locked in a desired angle, and the mechanical hand can be actuated for opening and closing. Accordingly, in some aspects, the upper limb prosthesis can have substantial weight, such as, for example, about forty to fifty pounds. The functional prosthesis can be configured to interface with residual nerves of the user 100 for actuating the actuator(s). For example, the prosthesis can comprise a prosthetic sensor that can sense electromyographic (EMG) signals. Accordingly, exact positioning of the socket 12 can be essential to communication between the residual nerves of the user and the prosthesis. Thus, the harness 20 can provide sufficient straps and anchor points to align the prosthetic sensor with each user's post-surgical neuromuscular status.

In an exemplary aspect, the prosthesis 10 can be a hybrid prosthesis with a body-powered elbow as is known in the art. The user can use a lift assist incorporated into the body-powered elbow to ballistically move the elbow into flexion, or the user can bend forward at the waist and the elbow can move the elbow into flexion. Once the user locks the elbow into the position she needs for function, the user can use electromyographic (EMG) input from one muscle to open and close her myoelectric hand. For example, contraction of the muscle can open the hand, and relaxation of that same muscle can close the hand.

In further aspects, the upper limb prosthesis 10 can be a passive prosthesis that can be provided for aesthetic purposes. Accordingly, in some aspects, the upper limb prosthesis can physically resemble a natural arm.

It is contemplated that the socket 12 can be a portion of (e.g., be integral to) the prosthesis. In further aspects, the socket 12 can be releasably coupled to the prosthesis 10. In this way, one or more prostheses can be coupled to the socket. That is, it is contemplated that the same socket and harness can be selectively coupled to and decoupled from a plurality of different prostheses.

In various aspects, the upper limb prosthesis 10 can be configured for a shoulder-level residual limb (e.g., from amputation of an arm at shoulder level). In further aspects, the upper limb prosthesis 10 can be configured for a user having a humeral amputation (e.g., below the shoulder-level). In exemplary aspects, the upper limb prosthesis 10 can be for a user with mid- to short transhumeral, shoulder, or interscapulorthoracic amputation.

In exemplary aspects, the harness 20 can be coupled to the socket 12 of the upper limb prosthesis 10. The harness 20 can comprise a front portion 22 that is configured to extend across the chest 104 of the user and receive at least a portion of the breasts 108 of the user therein. The front portion 22 can have opposed lateral sides 24. The front portion 22 can comprise a chest portion 50 that defines a cup area 52. In some aspects, the cup area 52 can comprise an area (e.g., an expanded area) of the chest portion 50 that serves to receive the breasts without separation of each breast so that a single receptacle can be configured to receive the breasts simultaneously without any internal divisions. In further aspects, the chest portion 50 can comprise cups 54 that encapsulate portions of the breasts. Optionally, the cups 54 can be positioned between an inner layer and an outer layer of fabric. In some optional aspects, the harness 20 can comprise underwire. In further aspects, the harness 20 can omit underwire. The harness 20 can comprise respective first and second sides that correspond to the first and second sides 6, 8 of the prosthesis system 4.

The harness 20 can further comprise a back portion 26 that is configured to extend across the back 102 of the user 100 and couple to the opposed lateral sides 24 of the front portion 22. Optionally, the front and back portions 22, 26 can be integrally formed. In exemplary aspects, the back portion 26 can comprise a back strap 28.

The harness 20 can further comprise a support strap 30 having a first end 32 and a second end 34. The first end 32 of the support strap 30 can couple to the socket 12 of the prosthesis 10 at a first anchor point 36. The second end 34 of the support strap 30 can couple to the back portion 26 on the second side 8 of the prosthesis system 4. The support strap 30 can be configured to distribute the load of the prosthesis 10 to other portions of the harness 20 (e.g., the front and back portions 22, 26 below the armpit of the intact arm) that, in turn, distribute the load to a large surface area of the user. In exemplary aspects, the support strap 30 can form an angle θ relative to a transverse plane 70 of less than 45 degrees, or less than 35 degrees (e.g., about 30 degrees). Said transverse plane 70 can be horizontal when the user 100 is sitting or standing up upright. It is contemplated that the exact angle θ relative to a transverse plane 70 can vary slightly among users depending on specific body dimensions and anatomical features. Optionally, in exemplary aspects, by using functional materials as further described herein (e.g., sports bra material), it is contemplated that the harness can provide adequate support using only a single support strap. However, it is contemplated that multiple support straps can be used together in some embodiments.

In exemplary aspects, the first anchor point 36 can optionally be on a front portion of the socket 12 (see, e.g., FIGS. 7 and 10), on a rear portion of the socket, or on a middle portion of the socket between the front and the rear portions of the socket.

In some aspects, where present, the support strap 30 can have an adjustable length. For example, the support strap 30 can extend through a buckle 45 (e.g., a buckle attached to the chest portion 50) and double back (e.g., reverse direction) to couple to itself (e.g., via hook and loop, one or more snaps, hooks, or other attachment elements). In further aspects, the support strap 30 can be non-adjustable so that, once fitted to a particular user, the position of the harness does not undesirably move. In exemplary aspects, the support strap 30 can be a portion of a bra (e.g., a back strap of a bra) or a material similar to that of a bra that is coupled to another bra to define a portion of the harness.

In some optional aspects, the harness 20 can comprise a first shoulder strap 40 that is configured to extend over the shoulder proximate to the residual limb 110. For example, the first shoulder strap 40 can extend between the chest portion 50 and the back strap 28. Optionally, the first shoulder strap 40 can be entirely positioned on the first side 6 of the prosthesis system 4. In further aspects, the first shoulder strap 40 can extend to the second side 8 of the prosthesis system 4 across the back of the user. Optionally, the harness can comprise a plurality of back straps that extend across the back of the user. The back straps can extend vertically, horizontally, or both (e.g., diagonally) to advantageously distribute the weight of the prosthesis to various other parts of the bra (and the body of the user).

In some optional aspects, the harness 20 can comprise a second strap 42 that is configured to extend over the shoulder opposite to the residual limb 110. For example, the second shoulder strap 42 can extend between the chest portion 50 and the back strap 28. Optionally, the second shoulder strap 42 can be entirely positioned on the second side 8 of the prosthesis system 4. In further aspects, the second shoulder strap 42 can extend to the first side 6 of the prosthesis system 4 across the back of the user. For example, optionally, the first and second straps 40, 42 can cross each other across the back of the user.

In some aspects, where present, the first shoulder strap 40 and second shoulder strap 42 can each have an adjustable length. For example, the shoulder straps can each comprise a strap portion that extends through a buckle 45 and doubles back (e.g., reverses direction) to couple to itself (e.g., via hook and loop, one or more snaps, hooks, or other attachment elements). In further aspects, the shoulder straps can be non-adjustable so that, once fitted to a particular user, the position of the harness does not undesirably move.

In exemplary aspects, where present, the first and second straps 40, 42 can define portions of the front portion 22 and portions of the rear portion 26 of the harness.

In some aspects, the harness 20 can comprise two anchor points, three anchor points, or more than three anchor points. For example, the harness 20 can comprise a second anchor point 46 that is provided within a respective interface region 44 between the front portion 22 of the harness and the socket 12. For example, at the second anchor point 46, the socket 12 can couple to the chest portion 50, the first shoulder strap 40, or a coupling member 51 that couples to and extends from the chest portion 50 and across a portion of the socket 12.

In further aspects, the harness 20 can comprise a third anchor point 48 (FIG. 8) that is provided within a respective interface region 44. The third anchor point 48 can optionally be between the front portion 22 of the harness 20 and the socket 12. For example, the third anchor point 48 can be between the socket 12 and a front portion of the first shoulder strap 40 that defines a portion of the front portion 22 of the harness 20. In further aspects, the third anchor point 48 can be provided between the rear portion of the harness 20 and the socket 12. For example, the third anchor point 48 can be between the a rear portion of the first shoulder strap 48 that defines a portion of the rear portion 26 of the harness 20.

It is contemplated that the anchor points can be positioned on a case-by-case basis based in the needs and structure of the user fitted for the prosthesis system 4. In some aspects, the user can, based on feeling, provide recommended locations for anchor points.

In yet further aspects, one or more coupling members 51 can extend from various portions of the harness to couple to the socket 12. In various aspects, the coupling members 51 can be flexible or rigid. Optionally, a portion of the coupling members 51 can be rigid and a portion of the coupling members can be flexible.

Optionally, each anchor point (e.g., the first, second, and third anchor points 36, 46, 48) can comprise a respective rivet 56 that couples the harness 20 to the socket 12. In further aspects, the anchor points can comprise other fasteners, such as, for example and without limitation, screws, snaps, and the like. The harness 20 can be configured to be decoupled from the socket 12 in order to allow the harness to be washed.

In various aspects, a plurality of harnesses 20 can be provided. The plurality of harnesses can be different colors and/or shapes for different aesthetics or different functions. The user can thus select the particular harness for a particular outfit or for a particular activity.

Optionally, at least a portion of the harness 20 can comprise functional clothing. That is, conventional clothing not intentionally formed for the purpose of a harness can be integrated into the harness 20. The functional clothing can be, for example a bra (e.g., a heavy sports bra), an athletic shirt, an athletic bra-shirt combination, a vest, a unitard, etc. For example, an off-the-shelf sports bra (e.g., a bra made by SHEFIT of Hudsonville, Mich.) can be adapted for use as a portion of the harness 20. In these aspects, features of a sports bra can be adapted for use as a portion of the harness. For example, the harness can comprise materials of a performance sports bra, such as, for example, spandex and polyester.

In exemplary aspects, the front portion 22 and the back portion 26 of the harness 20 can cooperate to define a loop 58 that is configured to extend about the torso 102 of the user 100. The harness 20 can comprise a closure 60 that adjoins the loop 58 at opposed first and second ends 62, 64 of the loop, wherein the closure is configured to selectively decouple the first and second ends of the loop. In this way, the closure 60 can be uncoupled (e.g., opened) to doff the harness 20 and re-coupled (e.g., closed) to don the harness. Optionally, the closure can comprise a zipper. In further aspects, the closure can comprise a magnetic coupling. For example, the closure can comprise one or more magnets with opposed polarity that have sufficient attraction to maintain the closure in a coupled state while using the harness but can allow the user to remove the harness with one hand. In further aspects, the closure can comprise a zipper, one or more hooks and eyelets, or hook and loop fastener, or any other suitable closure element.

In some aspects, the loop 58 can have an operative circumference, and the harness 20 can comprise an adjustment element that is configured to adjust the operative circumference of the loop. For example, in some aspects, the back strap 28 can be adjustable. In one aspect, the back strap 28 can extend through a buckle 66 and loop backward (in an opposite direction) to couple to itself (e.g., via hook and loop, one or more snaps, hooks, or other attachment elements). In further aspects, the operative circumference can be adjustable from accessing a fastener on the front portion of the harness to allow the user to more easily perform adjustments. For example, the harness can comprise hook (or loop) material on a strap that extends through a buckle and doubles back to couple to loop or hook material) on the front portion 22 of the harness. Other suitable fasteners for such adjustments to the operative circumference of the loop 58, such as, for example, hooks and eyelets, snaps, etc., are contemplated.

Similarly, while the first and second straps 40, 42 are shown extending and looping through the buckles 45 that are fixedly attached to the front portion 22 of the harness 20, in further optional aspects, the first and second straps 40, 42 can optionally loop through buckles that are coupled to the back portion of the harness 26 so that the user can pull and adjust the straps forwardly to tighten the first and second straps 40, 42.

The closure 60 can optionally be positioned on the front portion 22 of the harness 20. In this way, the user can easily reach the closure herself. For example, the closure 60 can be centered along the chest portion 50 (e.g., between the breasts). In further aspects, the closure 60 can be positioned to (e.g., offset toward) the first side 6 or the second side 8. In yet further aspects, the closure 60 can be positioned on the back portion 26.

In various aspects, at least a portion of the harness can be elastic. In some aspect, elasticity of different elements of the harness can vary. For example, optionally, the chest portion 50 can be more elastic than the support strap 30.

Accordingly, in some aspects, the harness 20 can comprise a bra. It is contemplated that the bra can at least partially support the weight of the prosthesis. The bra can disperse the load of the prosthesis by increasing the area of the body surface(s) supporting the weight as compared to conventional harnesses, while also distributing the load to locations that optimize comfort of the wearer (e.g., areas other than the armpit of the intact arm). For example, it is contemplated that the bra can include suspension straps that are integrated into the bra (or other suitable garment). Further, the fabric and other technology of the bra can provide other advantages. Still further, the load can be distributed so that the breasts and other tissue and skin areas of the user are not compressed in an aesthetically unpleasing manner. In this way, the harness can be more comfortable and aesthetically pleasing than conventional harnesses and can reduce or eliminate tissue damage in the breast and armpit areas of the user. The advantages of the harness as disclosed herein can reduce prosthesis abandonment (e.g., the unwillingness of an individual to continue use a prosthesis). Optionally, in exemplary aspects, when in use, it is contemplated that the harness can avoid positioning of material underneath the residual arm (e.g., armpit) of the subject.

In various embodiments, the bra (or the harness) can be configured to fit a female torso. In further aspects, it is contemplated that the bra (or the harness) can be configured to fit a male torso.

The one or more coupling members 18 that couple the bra 12 to the socket 14 can comprise one or more rigid coupling members. In further aspects, the one or more coupling members 18 can comprise flexible straps. The coupling members 18 can be configured to be decoupled from the bra. This can advantageously allow the bra to be washed. The coupling members 18 can couple to the bra via snaps, hook and loop, hinges, or any suitable fastener. Optionally, one or more of the coupling members 18 can have adjustable lengths. For example, at least one of the fasteners can comprise a buckle that enables the user (or physical therapist or an assistant) to select the length of the coupling member. It is contemplated that the coupling members 18 can optionally be customized, both in length and attachment locations on the bra and socket, for the particular user. Accordingly, the configuration of the harness can be determined under the guidance of a physician, physical therapist, or occupational therapist.

Figure 4:
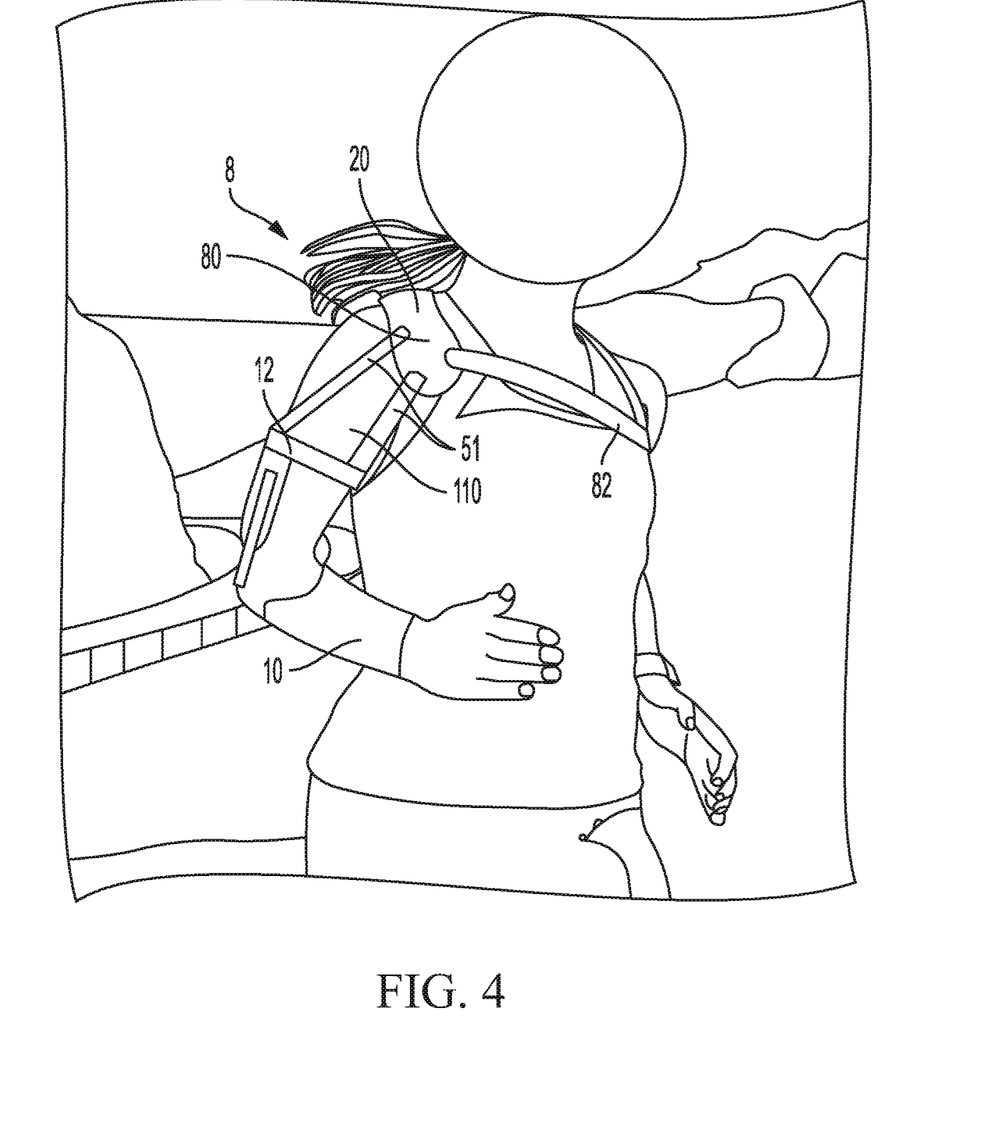
FIG. 4 is a perspective view of a harness in accordance with embodiments disclosed herein.
Figure 5:
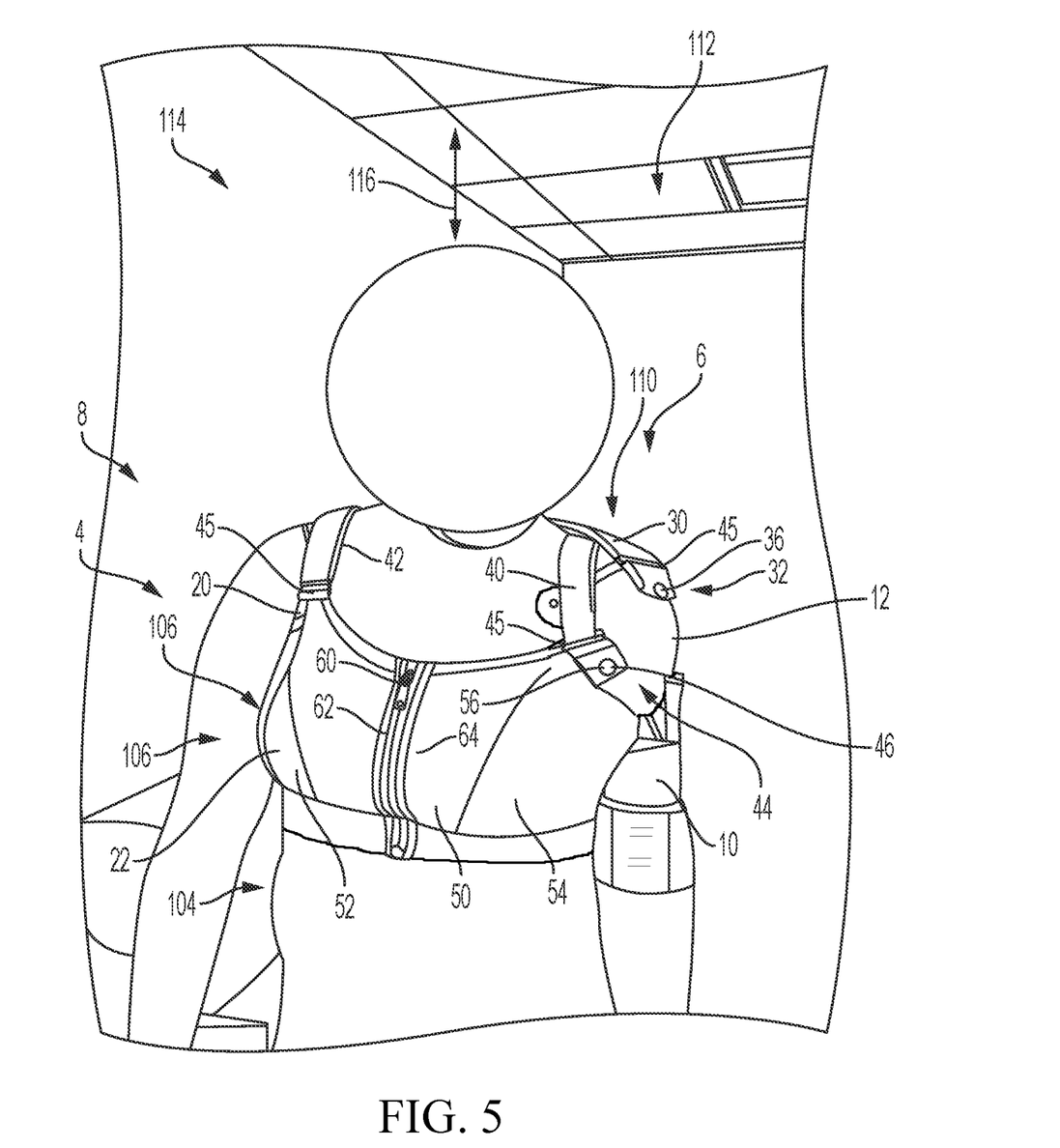
FIG. 5 is a front view of an exemplary prosthesis system in accordance with embodiments disclosed herein.
Figure 6:
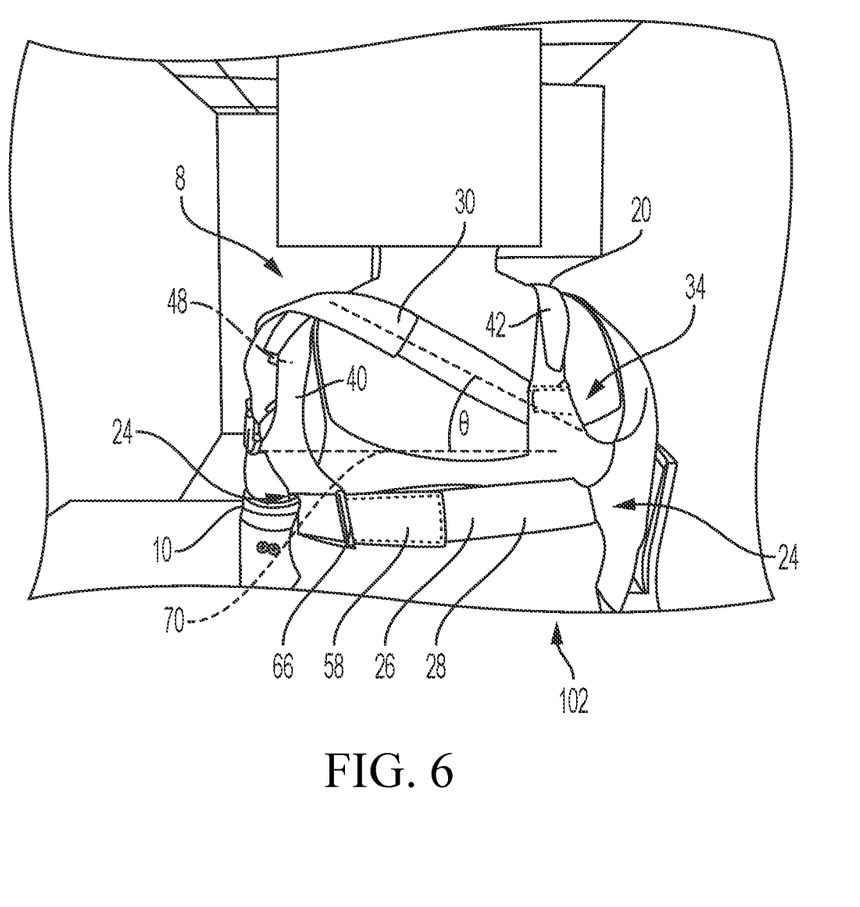
FIG. 6 is a rear view of the exemplary prosthesis system of FIG. 5.
Figure 7:
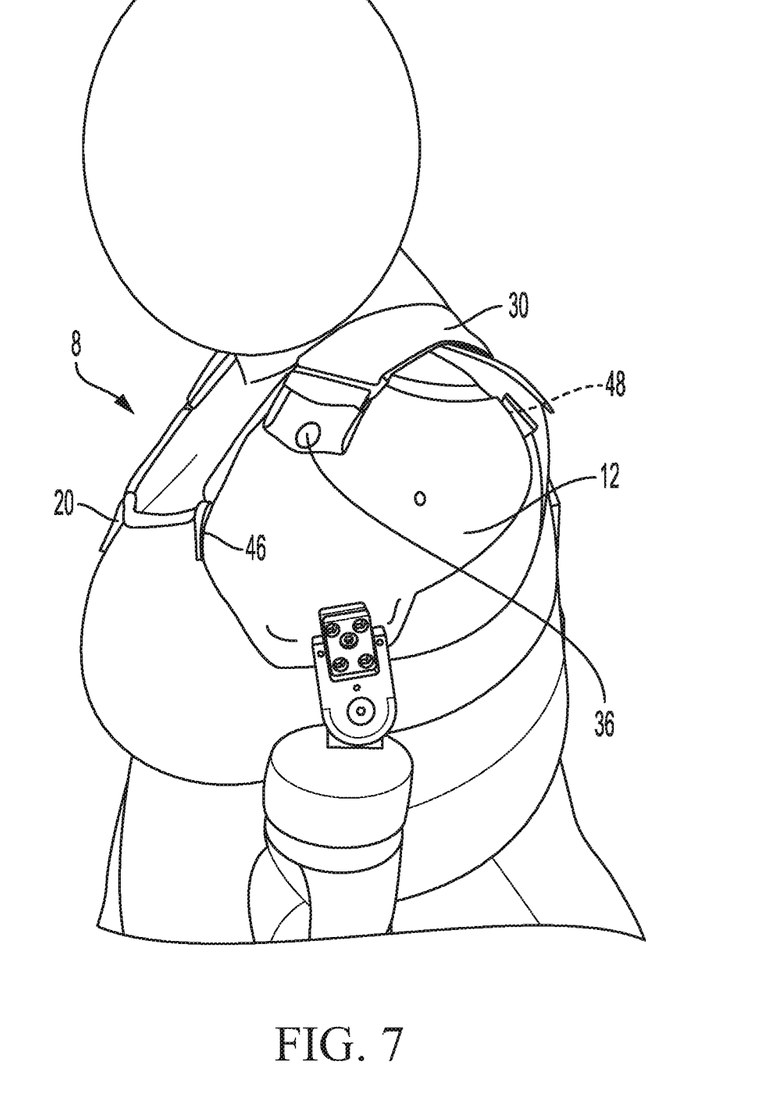
FIG. 7 is a side view of the exemplary prosthesis system of FIG. 5.
Figure 8:
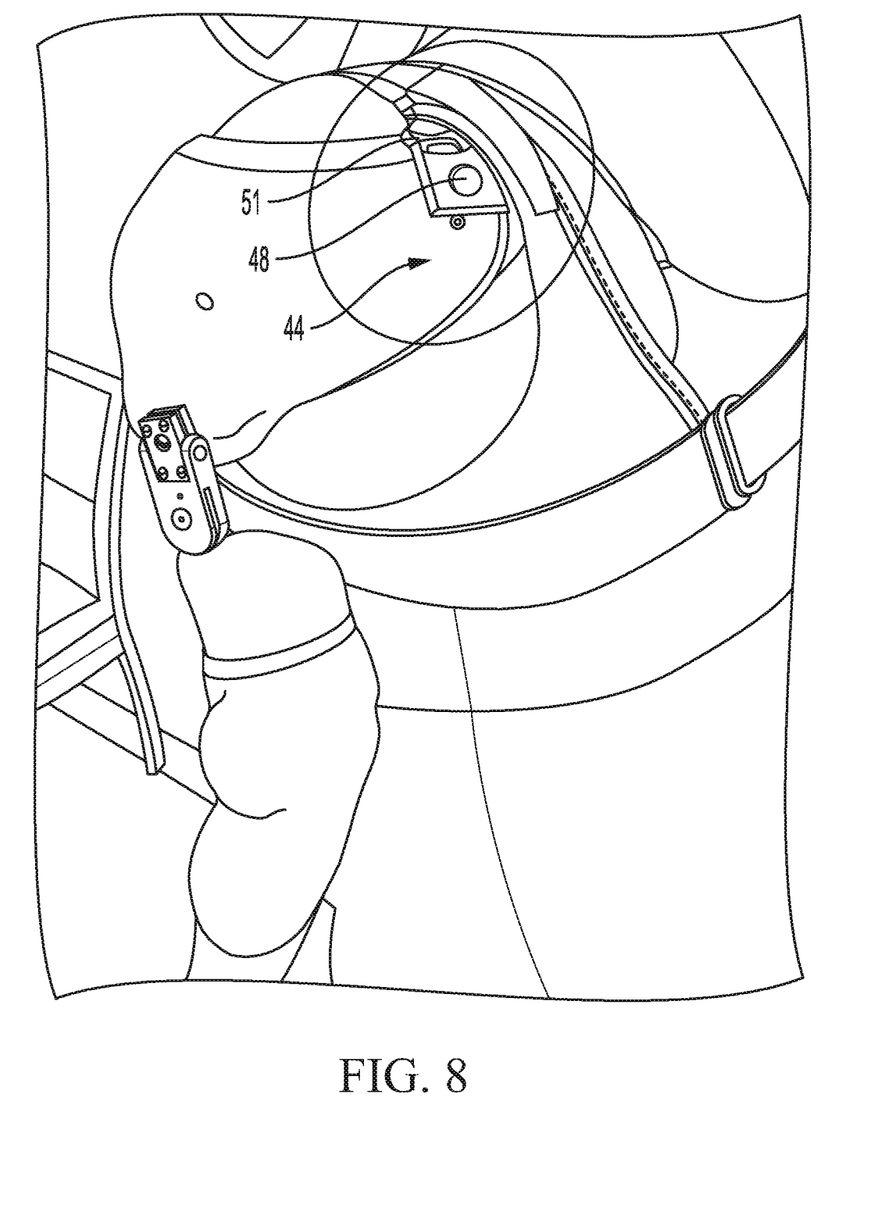
FIG. 8 is a rear perspective view of the exemplary prosthesis system of FIG. 5 with a support strap removed to show a rear anchor point.
Figure 9:
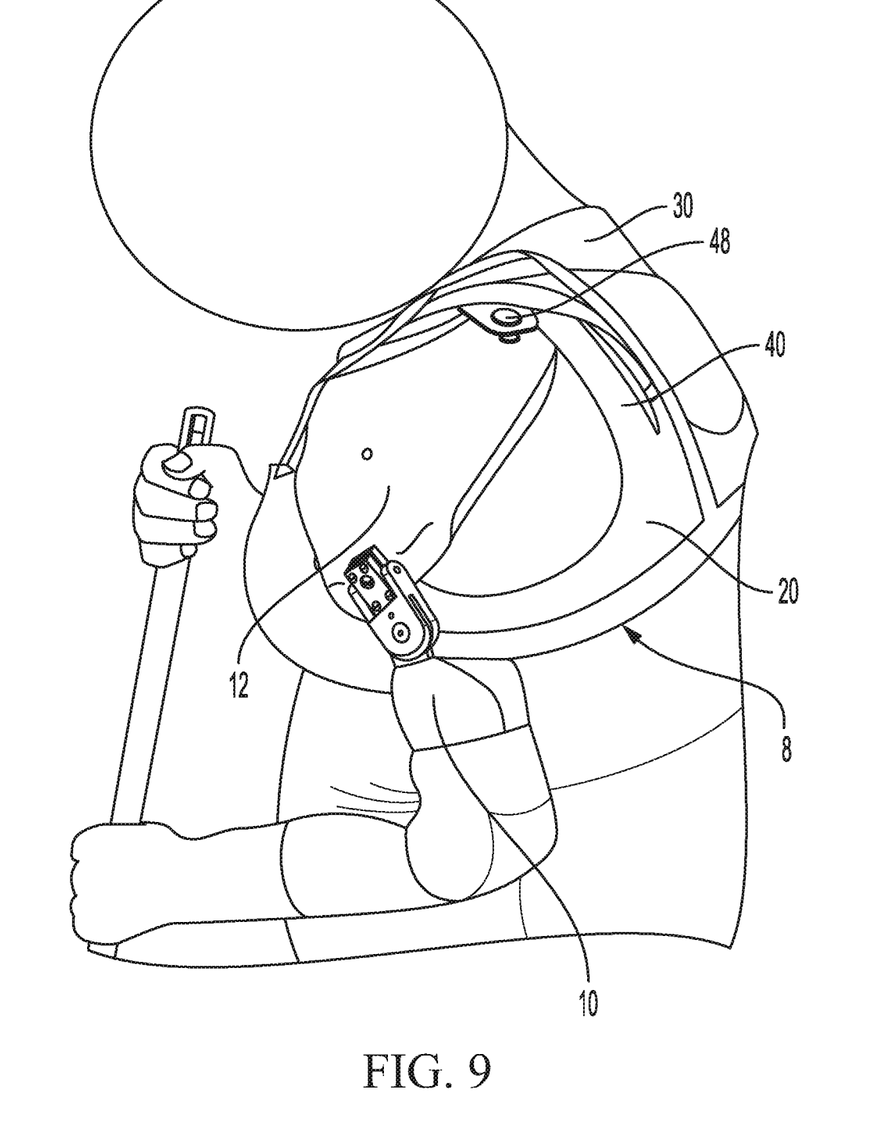
FIG. 9 is a rear perspective view of the exemplary prosthesis system of FIG. 5 during functional use.
Figure 10:
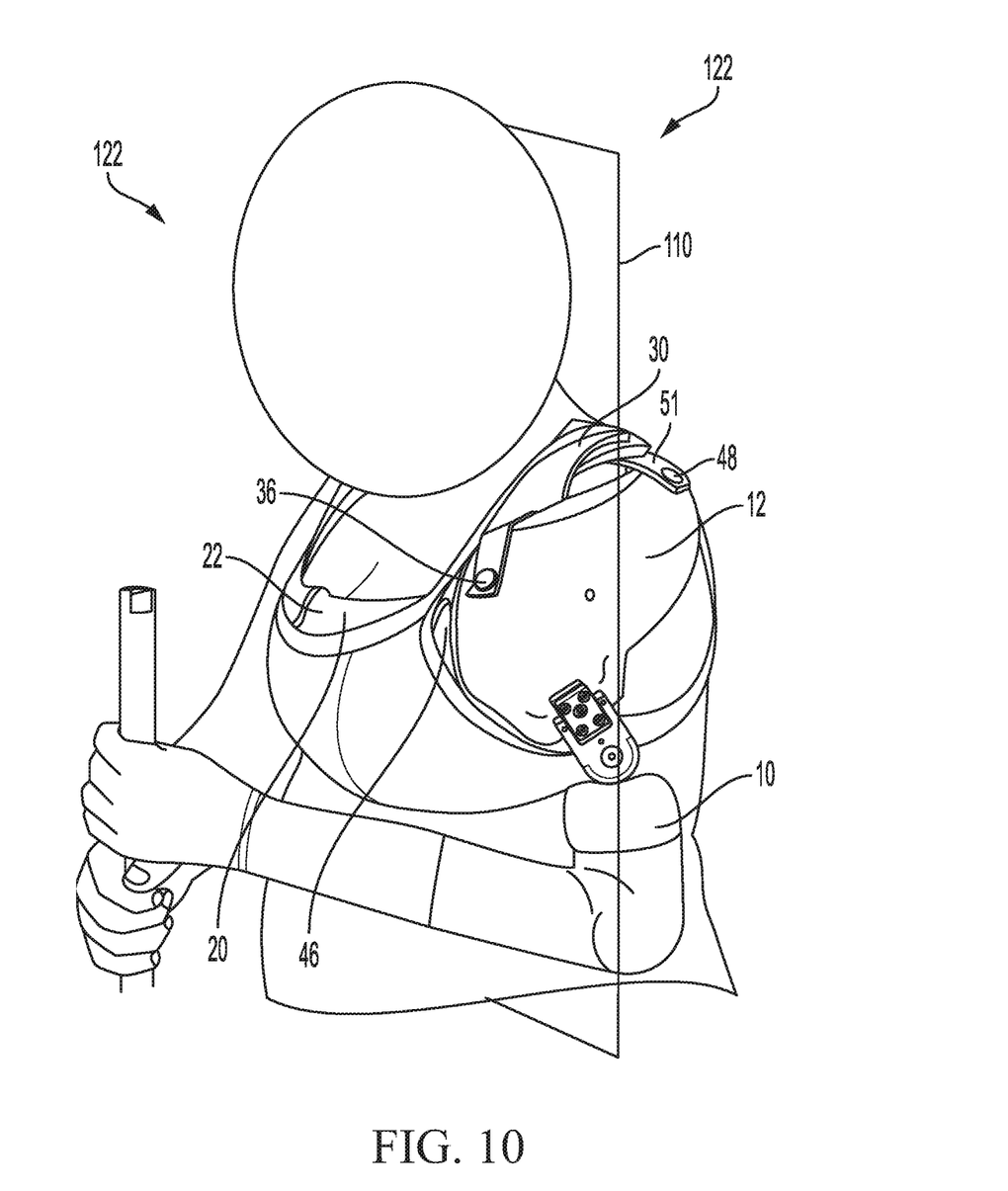
FIG. 10 is a front perspective view of the exemplary prosthesis system of FIG. 5.

Referring also to FIG. 4, in some optional aspects, the harness 20 can comprise a shoulder pad 80 that is configured to bias against the shoulder of the user and further support the prosthesis. One or more coupling members 51 can extend between, and couple to, the shoulder pad 80 and the socket.

In some optional aspects, the harness 10 can comprise a chest strap 82 that extends across the chest of the user. It is contemplated that the chest strap 82 can be configured to extend above the breasts of the user or below the breasts of the user (but not directly across the breasts of the user). Optionally, the chest strap 82 can couple to the bra and/or the shoulder pad 80.

In further optional aspects, the harness 20 can comprise a neck strap 86 (FIG. 3) that is configured to extend across the back of the neck of the user. Optionally, the neck strap can comprise a loop through which the opposing intact arm of the user extends so that the neck strap biases against the armpit of the opposing intact arm of the user.

It is contemplated that the disclosed prosthesis system 4 can be assessed and optimized using pressure mapping. The pressure mapping can use a plurality of sensors to determine pressures at different locations. Pressures can be mapped at the socket-residual limb interface as well as between the harness 20 and the patient (e.g., at the underarm and shoulder areas of the intact arm).

For example, the pressure sensors can be positioned on (optionally, adhered to the skin using double-sided tape). In some aspects, the sensors can be outside and not engaging the socket or any prosthetic componentry. The positioning of the sensors can be done before the prosthesis is donned to allow the sensors to be fixed securely and consistently over the regions of interest (whether that is on the residual limb to measure the socket interface pressures or under the axilla to measure harness pressures). When the prosthesis and harness are donned, the pressures that result can be measured. For example, a scanner (e.g., a VORUM scanner) can be used to register the 3D location of sensors and relevant anatomical landmarks. This data can be associated with the sensor pressure readings to provide a 3D map of pressures occurring on the body.

Prosthesis fit, suspension, and comfort are three factors that are directly related to the pressure distribution developed at the interface between the prosthesis and the user's body. Pressure distributions can be characterized as participants wear the prosthesis system. In some aspects, a TEKSCAN VERSATEK system (or other scanning system) can allow for measurements of pressures at two simultaneous locations across the body. Pressure development between the prosthetic socket and residual limb can be quantified to characterize socket fit and changes in suspension, as well as around the contralateral axilla, an area that often bears prosthetic related loads and is commonly associate with discomfort in female prosthesis users. At each location, a sensor (e.g., a TEKSCAN 9811E sensor) can be used. The sensor can be a "paper thin," flexible sensor that can be trimmed to match anatomical contours and provide discrete pressure measurements. The sensors can be provided on the skin to securely cover each participant's residual limb and in the contralateral axilla region.

Pressure measurements can then be performed in which, (1) pressure is measured wearing the prosthetic liner with the residual limb positioned neutral at their side, (2) wearing prosthesis with 90 degrees prosthetic elbow flexion, and (3) full elbow extension with shoulder flexion in the plane of the scapula.

Using computer software such as MATLAB and Paraview software, sensor placement data and the pressure measurement data can be imported to create color-coded 'heat maps' that directly link pressure values to the three-dimensional anatomy of each participant. Using threshold filters and numerical integration regions of particular interest (ex. regions where control electrodes must firmly contact the tissue) can be isolated, as well as regions developing maximum pressures, and their surface areas can be calculated. For each user, maximum and mean pressures, the anatomical regions developing these values, and the surface areas which they are distributed across can be compared when wearing the prosthesis system. In this way, the system can be fitted for a user to more equally distribute pressure across the contralateral axilla and thorax regions over larger surface areas.

Other user feedback for fitting can include satisfaction, measured with the Orthotic Prosthetic Users Survey (OPUS) Satisfaction with Device Scale (Appendix 4), function, measured with the OPUS Upper Extremity Functional Status Scale (Appendix 5) and comfort, measured with the Socket Comfort Score, a numeric rating 0-10 scale where 0 is the least comfortable and 10 the most comfortable.

The prosthesis system can be configured for use (e.g., comfortable use) for at least one hour (e.g., one continuous hour) per week, at least one hour (e.g., one continuous hour) per day, several hours (optionally, continuous hours) per day, or more. The prosthesis system 4 can permit the same or a greater range of motion of the prosthesis than a conventional harness.

Various features of a functional clothing such as a bra that can advantageously be incorporated into the harness disclosed herein are provided in U.S. Pat. No. 10,568,367, granted Feb. 25, 2020, the entirety of which is hereby incorporated by reference herein.

Although the foregoing invention has been described in some detail by way of illustration and example for purposes of clarity of understanding, certain changes and modifications may be practiced within the scope of the appended claims.

What is claimed is:

1. A harness for coupling a prosthesis to a user having a back, a torso, a chest, breasts, and an upper residual limb on a first side of the user, the harness having opposing first and second sides divided by a sagittal plane, the first side of the harness corresponding to the first side of the user, said harness comprising:
   a front portion that is configured to extend across the chest of the user and receive at least a portion of the breasts of the user therein, wherein the front portion has opposed lateral sides;
   a back portion that is configured to extend across the back of the user and couple to the opposed lateral sides of the front portion;
   a support strap having a first end and a second end, wherein the first end of the support strap is configured to couple to a socket of the prosthesis at a first anchor point on the first side of the harness, wherein the second end is coupled to the back portion on the second side of the harness; and
   a second anchor point at which the front portion of the harness is configured to couple to the socket of the upper arm prosthesis,
   wherein the harness comprises a first shoulder strap that defines a portion of the front portion of the harness and a portion of the rear portion of the harness, wherein the harness comprises a third anchor point that is configured to couple the first shoulder strap to the socket of the upper arm prosthesis.

2. The harness of claim 1, wherein the harness comprises:
   a chest portion;
   a back strap; and
   a first shoulder strap that extends between and couples to the chest portion on the first side of the prosthesis system and the back strap.

3. The harness of claim 2, further comprising a second shoulder strap that extends between and couples to the chest portion on the second side of the prosthesis system and the back strap.

4. The harness of claim 1, wherein the front portion and the back portion of the harness cooperate to define a loop that is configured to extend about the torso of the user, wherein the harness comprises a closure that adjoins the loop at opposed first and second ends of the loop, wherein the closure is configured to selectively decouple the first and second ends of the loop.

5. The harness of claim 4, wherein the closure comprises a magnetic closure.

6. The harness of claim 4, wherein the closure comprises a zipper, at least one hook, or hook and loop fastener.

7. The harness of claim 4, wherein the closure is positioned on the front portion of the harness.

8. The harness of claim 1, wherein front portion and the back portion of the harness cooperate to define a loop that is configured to extend about the torso of the user, wherein the loop has an operative circumference, and wherein the harness comprises an adjustment element that is configured to adjust the operative circumference of the loop.

9. The harness of claim 1, wherein the front and back portions of the harness are integrally formed.

10. The harness of claim 1, wherein the harness comprises at least one anchor point, wherein the at least one anchor point comprises the first anchor point, wherein the harness further comprises a respective rivet at each anchor point of the at least one anchor point that is configured to couple the harness to the socket.

11. The harness of claim 1, wherein the front portion and the back portion are formed as a functional clothing item.

12. The harness of claim 11, wherein the functional clothing item comprises a sports bra.

13. The harness of claim 1, wherein, when worn by the user, the support strap is configured to form an angle relative to a transverse plane of less than 45 degrees.

14. The harness of claim 1, wherein the front portion of the harness comprises a first coupling member having a fixed length, wherein the second anchor point is positioned on the first coupling member.

15. The harness of claim 1, wherein the first shoulder strap comprises a second coupling member having a fixed length, wherein the third anchor point is positioned on the second coupling member.

16. A prosthesis system for a user having a back, a torso, a chest, breasts, a first side, an opposed second side relative to a sagittal plane, and an upper residual limb on the first side, said prosthesis system comprising:
   an upper arm prosthesis comprising a socket, the upper arm prosthesis being positioned on a first side of the prosthesis system corresponding to the first side of the user;
   a harness that is coupled to the socket of the upper arm prosthesis, the harness comprising:
      a front portion that is configured to extend across the chest of the user and receive at least a portion of the breasts of the user therein, wherein the front portion has opposed lateral sides;
      a back portion that is configured to extend across the back of the user and couple to the opposed lateral sides of the front portion;
      a support strap having a first end and a second end, wherein the first end of the support strap is coupled to the socket of the prosthesis at a first anchor point, wherein the second end is coupled to the back portion of the harness on a second side of the prosthesis system corresponding to the second side of the user, the second side of the prosthesis system being opposite the first side of the prosthesis system relative to the sagittal plane; and
      a second anchor point at which the front portion of the harness is coupled to the socket of the upper arm prosthesis,
      wherein the harness comprises a first shoulder strap that defines a portion of the front portion of the harness and a portion of the rear portion of the harness, wherein the harness comprises a third anchor point at which the first shoulder strap is coupled to the socket of the upper arm prosthesis.

17. The prosthesis system of claim 16, wherein the upper arm prosthesis is a passive prosthesis.

18. The prosthesis system of claim 17, wherein the upper arm prosthesis is a functional prosthesis.

* * * * *